(12) United States Patent
Tanimura

(10) Patent No.: US 6,224,761 B1
(45) Date of Patent: *May 1, 2001

(54) MULTISTAGE LIQUID-SOLID FRACTIONAL EXTRACTION APPARATUS

(76) Inventor: Takenori Tanimura, 3642-13, Shimonoshin, Toyama-shi, Toyama-ken (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/360,982

(22) Filed: Jul. 26, 1999

(30) Foreign Application Priority Data

Jul. 30, 1998 (JP) .................................................. 10-216164

(51) Int. Cl.[7] .................................................. B01D 15/08
(52) U.S. Cl. .................... 210/198.2; 210/511; 210/657; 422/261; 422/269
(58) Field of Search ................................ 210/657, 198.2, 210/511; 422/261, 269

(56) References Cited

U.S. PATENT DOCUMENTS

| | | | |
|---|---|---|---|
| 4,422,941 | * 12/1983 | Vaughan | 210/657 |
| 4,551,251 | * 11/1985 | Kolobow | 210/657 |
| 4,615,805 | * 10/1986 | Ito | 210/657 |
| 4,857,187 | * 8/1989 | Ito | 210/657 |
| 4,900,435 | * 2/1990 | Anderson | 210/657 |
| 4,900,446 | * 2/1990 | Anderson | 210/657 |
| 4,968,428 | * 11/1990 | Nunogaki | 210/657 |
| 5,024,758 | * 6/1991 | Ito | 210/657 |
| 5,087,369 | * 2/1992 | Tanimoto | 210/657 |
| 5,114,589 | * 5/1992 | Shibusawa | 210/657 |
| 5,217,608 | * 6/1993 | Conway | 210/657 |
| 5,273,656 | * 12/1993 | Anderson | 210/657 |
| 5,595,650 | * 1/1997 | Manz | 210/657 |

OTHER PUBLICATIONS

Snydec, Introduction to Modern Liquid Chromatography, John Wiley & Sons, Inc, 1979, pp. 203, 204, & 361.*

* cited by examiner

Primary Examiner—Ernest G. Therkorn
(74) Attorney, Agent, or Firm—Darby & Darby

(57) ABSTRACT

The object is to provide a multistage liquid-solid fractional extraction apparatus in which a separation procedure of a large amount of mixture can be carried out exactly and effectively in a simple procedure by use of a partition difference in liquid chromatography. The multistage liquid-solid fractional extraction apparatus comprises multiple containers 3 capable of accommodating liquid and solid for a liquid-solid extraction, a liquid inlet part 1 and a liquid outlet part 2 equipped with in each container, a pipe 4 to carry liquid from the liquid outlet part of the forward container to the liquid inlet part of the backward container, an efflux protecting device (filter 5) for solid, which is equipped with at the above liquid outlet part, and along with these a stirring device to let solid in said container move in liquid by virtue of the density difference between solid and liquid when rotating or swinging the container 3.

8 Claims, 4 Drawing Sheets

MULTISTAGE LIQUID-SOLID FRACTIONAL EXTRACTION APPARATUS

BACKGROUND OF THE INVENTION

The present invention relates to a multistage liquid-solid fractional extraction apparatus and more specifically, to a multistage liquid-solid fractional extraction apparatus used for separation of substance by making use of a difference in the adsorption power of the substance existing in solution to solid.

As a method to remove or to recover a substance in solution by means of its adsorption to solid, a decoloration by the active carbon, a removal of the ion by the ion-exchange polymer or the like are widely known. These procedures mostly finish in one step, however in case of separating each kind of substances by making use of the difference in each adsorption power to a specific solid, the chromatography is widely used. The chromatography is a technology in which a fine solid in a uniform shape is packed in the column, liquid or gas as a mobile phase is flowed therein, and a lot of substances existing in a solution or gas are separated by making use of a distribution difference of substances in between solid and liquid or between solid and gas, and is an extremely effective device which can carry out a mutual separation by making use of a small difference of the distribution coefficients in case of the separation of a small amount of mixture.

As described above, the chromatography is an effective separation device for separation of a small amount of mixture, but it cannot be said that it is an appropriate device for separation of a large amount of mixture. Namely, although a lot of trials have conventionally been done to separate a large amount of mixture by employing a chromatographic technique and by enlarging the column size, it has not been come yet.

In order to firmly carry out the separation of a substance by chromatography, it is necessary to uniformly flow a mobile phase in a solid phase packed in the column, and this is also the case when the column size is enlarged to treat a large amount of sample. However, in the case that the column size becomes larger and the cross section becomes wider, it becomes more difficult to make a resistance against fluid uniform in a wide cross section as a whole, giving a difference in a fluid resistance in the column, so that the flow rate becomes rapid at a place where the fluid resistance is small and the flow amount of the mobile phase becomes large at a part of the column cross section, i.e. a so-called channeling occurs. In such a case, the uniform flow of the mobile phase, which is a fundamental condition of the chromatography, is not achieved, and as a result of course, the separation efficiency deteriorates significantly.

Additionally, in case that a substance exists, which has a big adsorption power for solid and which scarcely elutes once it adsorbs, and that such substance is adsorbed by solid, passages become narrower by that extent and the resistance of the mobile phase against the flow increases, resulting to a change of the resistance against the mobile phase in each cross section of the column whenever a mixed sample is flowed. Therefore, even if the solid is initially packed uniformly, the flow resistance varies whenever a sample is flowed, and furthermore, the chromatographic procedure cannot directly be applied to the separation of a large amount of sample, since it is impossible to control the variation. Further, the fact that such a phenomenon does not occur in a usual chromatography is owing to the presence of only an extremely small amount of the irreversibly adsorptive substance, even if any, showing that a considerable number of treatments are possible until it affects the flow resistance of the column. In fact, in case of the analysis in the chromatography, it is widely known that a performance of the column degrades as the number of times of a sample injection increases.

Thus, although the chromatography is extremely effective as a separation device of a small amount of mixture, it is not possible to get a reproducible result in separation of a large amount of mixture, and there has been a big demand to develop a device by which a large amount of mixture can be separated in a similar procedure as a chromatography.

In such circumstances, this applicant previously provided a multistage liquid-solid fractional extraction apparatus by which a separation procedure for a large amount of mixture could firmly and effectively be carried out by making use of the distribution difference in the liquid chromatography. However, when a stirring apparatus such as a magnetic stirrer or screw as a stirring device, by which a liquid-solid mixture is directly stirred in a mechanical way, is employed, the solid (adsorbent) is ground by the friction with the stirrer or the like in a long lasting stirring procedure to a fine powder state, and possibly, a stable and constant state cannot be kept due to the flowing out from an efflux protecting device, for example, a filter or the like, which is equipped with at a liquid outlet part, or to the occurrence of the clogging. Further, in cases of employing a large volume of container or of a high solid concentration, the driving force becomes excessive, and the uniform stirring cannot be expected, whereby a deterioration of the stirring efficiency is anticipated.

SUMMARY OF THE INVENTION

Since the object of the above-mentioned stirring in a liquid-solid extraction apparatus is to let liquid and solid contact uniformly and effectively, it is desirable that the liquid and solid mutually move as uniformly as possible.

Thus, the present invention resides in providing a multistage liquid-solid fractional extraction apparatus which can effectively stir the liquid and solid, so as to firmly and effectively carry out a separation procedure of a large amount of mixture by means of a simple operation making use of a distribution difference in the liquid chromatography, and can keep a long standing stable steady state while suppressing the pulverizing of the solid.

To achieve the above object a multistage liquid-solid fractional extraction apparatus of the present invention is characterized in that it comprises multiple containers capable of accommodating liquid and solid subjected to a liquid-solid extraction, a liquid inlet part and a liquid outlet part both equipped with in each container, a carrying device to carry the liquid from the liquid outlet part of the forward container to the liquid inlet part of the backward container, a stirring device to rotate or swing said containers to move the solid in the liquid by means of the density difference between solid and liquid, and an efflux protecting device for solid, which is equipped with at the above liquid outlet part.

Namely, the present invention resides in that the stirring to accelerate a contact of liquid with solid in each container of the multistage liquid-solid fractional extraction apparatus is carried out by making use of a density difference between liquid and solid. That is, since the solid usually has a density different from that of the liquid, the solid moves in the liquid by the gravity, when a container is overturned. Likewise, it is also possible to stir liquid and solid in a container by rotation or swing of the container per se.

BRIEF DESCRIPTION OF THE DRAWINGS

Preferred embodiments of the present invention will be described in detail with reference to the following figures.

DETAILED DESCRIPTION OF PREFERRED EMBODIMENTS

Figure 1D:
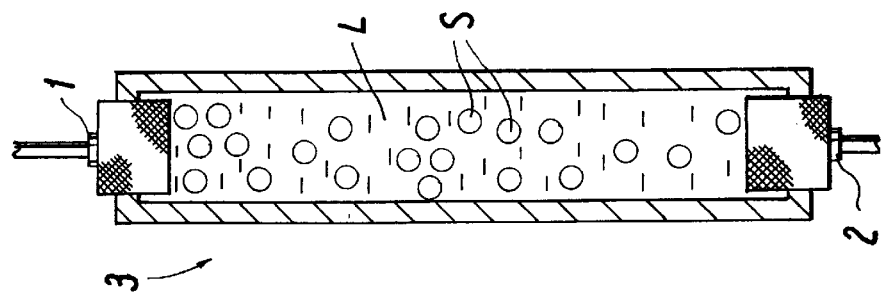
FIGS. 1A, 1B, 1C, and 1D, This is the cross section showing one example of embodiments of the multistage liquid-solid fractional extraction apparatus according to the invention.

FIG. 1 is the rough figure showing one example of embodiments of the multistage liquid-solid fractional extraction apparatus according to the invention. One constitutional unit of the multistage liquid-solid fractional extraction apparatus is a sealable container 3 having the inlet part 1 and the outlet part 2 of the liquid as a mobile phase, and the multistage liquid-solid fractional extraction apparatus is constructed by connecting the liquid inlet part 1 and the liquid outlet part 2 of a lot of containers 3 by the pipe 4 which is a carrying device of liquid. In the outlet part 2 of liquid, for example, a mesh type filter 5 is provided as an efflux protecting means to protect solid in the container 3 for flowing out together with liquid. Further, it is not necessary to provide a filter at the liquid inlet part 1, but it is possible to exclude the directivity of the container 3 by providing the same filter at the inlet part 1 as well.

Figure 2:
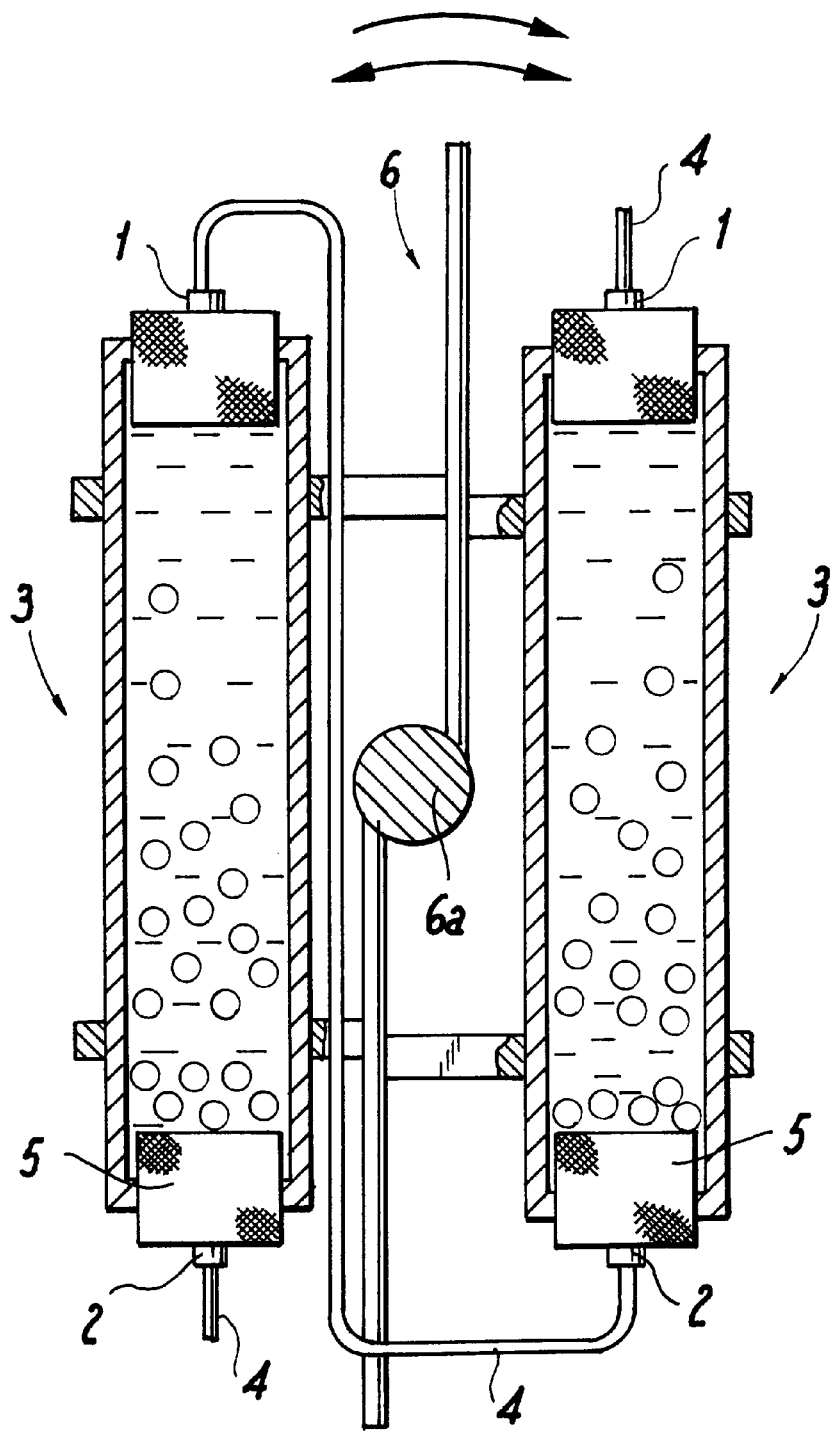
FIG. 2: This is the rough figure showing one example of embodiments wherein a plural number of containers are settled to the stand which rotates or swings.
Figure 3:
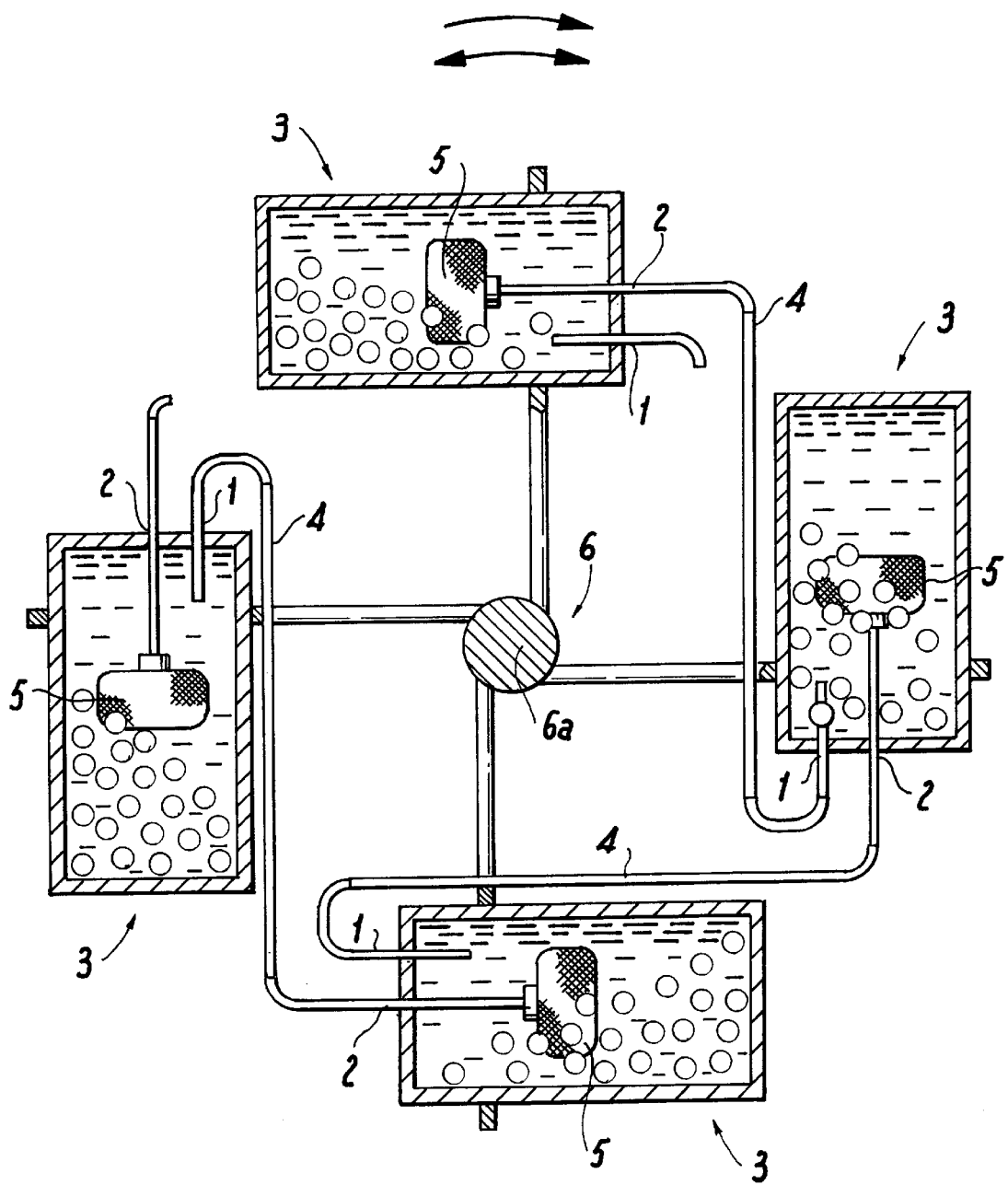
FIG. 3: This is the rough figure showing another example of embodiments wherein a plural number of containers are settled to the stand which rotates or swings.

As shown in FIG. 2 and FIG. 3, a plurality of containers 3 are respectively set up to the stand 6 which holds and can rotate or swing the containers, and each container is connected in series by the pipe 4. The containers 3 are rotated or swinged at an appropriate speed in connection with the axis 6a of this stand 6 to a driving device such as a motor or a crank, so that solid in the container moves in liquid by virtue of the density difference from liquid, accelerating a substance equilibrium partition between solid and liquid.

Figure 1C:
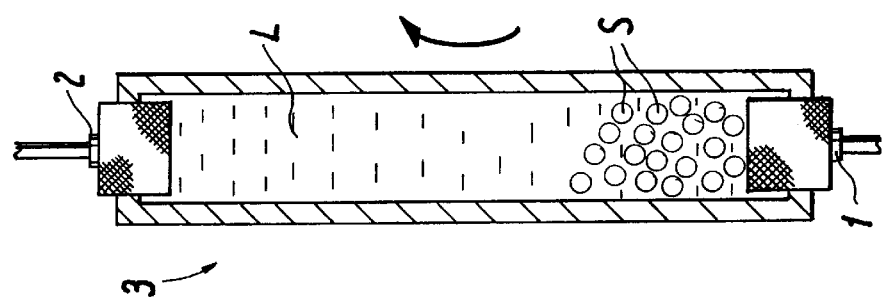
Figure 1B:
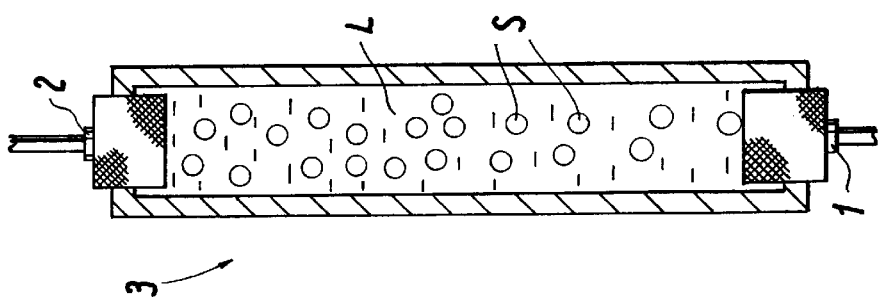
Figure 1A:
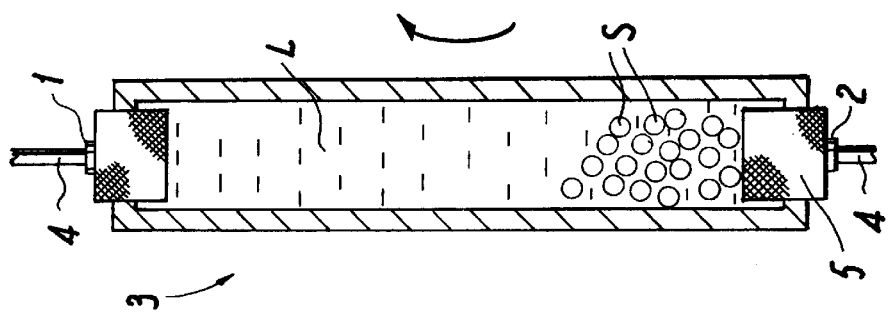

For example, as shown in FIG. 1(A), in the case that the density of the solid S is larger than that of the liquid L, the container 3 is positioned, so as to be the liquid inlet part 1 up, resulting to the state that the solid S sinks downward to the outlet part 2 of the container 3. When said container 3 in this state is rotated and the liquid outlet part 2 is directed upward as in FIG. 1(B), the solid S gradually sinks in the liquid L due to the density difference. Additionally, as shown in FIG. 1(C), in case that the inlet part 1 is directed upward as in FIG. 1(D) by rotating again the container 3 when the solid S sinks to the side of the inlet part 1, the solid S sinks toward the outlet part 2, and returns to the state of FIG. 1(A).

Consequently, by changing the up-down direction of the container 3 by rotation or swing of the container 3 at an appropriate timing, solid moves up and down within liquid, whereby liquid and solid become in a stirred state. Since the external force toward solid is extremely little in such a stirred state compared with the case where the solid is forcibly stirred by a stirrer or the like, the solid is hardly destroyed by a friction force or an impact. Further, comparing the rotation with the swing, the rotation is superior in the stability in that the direction of the mechanical movement is constant, whereas the swing is superior in that a rotatory seal is not needed for plumbing of liquid.

Each container 3 is filled with e. g. an appropriate amount of adsorbent as a solid, and a liquid as a mobile phase and then sealed. When a mobile phase solution is supplied at an optional amount of flow from the liquid inlet part 1 of the starting container while rotating or swinging the container 3 at this state, a volume of liquid corresponding to a liquid amount supplied flows out from the liquid outlet part 2. At this time, the amount of substance existing in the liquid flowing out of the container 3 is expected to be in a partition equilibrium state against the adsorbent. Therefore, in an ideal case, one container 3 corresponds to one plate in the plate theory of the chromatography. Accordingly, e. g. 10 pieces of containers are connected, a separation system corresponding to 10 plates of the chromatography is to be formed as a matter of course.

In this case, in order to make each connected container 3 to a uniform condition, the amount of adsorbent and the volume of liquid in each container are to be constant. Since a partition equilibrium is carried out by rotation or swing of the container, partition conditions for a specific substance (solute) in each container, that is, stationary phase volume, mobile phase volume, partition coefficient or distribution coefficient, become constant, and meet conditions of the theoretical plate. Further, since the partition is made by stirring in the theoretical plate, a constant chemical property is needed. However, the uniformed shape is not needed unlike the adsorbent of the chromatography. It is also no longer necessary to uniformly pack the adsorbent like in the column, because the adsorbent can uniformly be mixed by rotation or swing of the container. Further, a concentration difference is small since a mobile phase moves the next container after the partition equilibrium is attained. As such, three fundamental conditions of the chromatography can be excluded, that is, to use a uniform size and shape of adsorbent, to uniformly pack and to uniformly flow a mobile phase into the column.

In addition, if a partition of the solute is only carried out efficiently enough by transfer of the solid with rotation and swing of the container, a large scale operation is possible because of no limitation to the volume of the container. Further, as it also has characteristics that the volume ratio between adsorbent and liquid can be adjusted to an appropriate ratio for separation of an aimed substance, there is no such limitation that the volume ratio between adsorbent and liquid should be restricted at certain value, unlike when packing spherical solid into the column.

On the other hand, a column having theoretical plates exceeding several thousands of plates is as a rule used in chromatography, and also, the above-mentioned multistage liquid-solid fractional extraction apparatus needs several thousands of containers because containers corresponding to at least theoretical plates must be connected.

Accordingly, it seems practically difficult to provide a high separation performance because it is necessary to set up a huge apparatus and to connect several thousands of containers to carry out the separation of mixture. However, the separation by chromatography are mostly carried out for multiple components, whereas, in most cases of separation for a large amount of mixture, a specific single component is simply isolated or only two components are separated.

Coming across a process to carry out separation on the column of chromatography, it can be said that the separation of an aimed substance from the other substances is carried out around the position of the aimed substance on only a part of the column, and the other part is only a flow route of mobile phase. Therefore, if an apparatus, in which only this band part necessary for separation is used, is available, an efficient separation operation can be carried out without use of a lot of containers. Such an apparatus can be constituted, for example, in the following.

First, in case of the separation purification of only one component, a system connecting a plural number of containers is prepared, and a sample is put into a container at one end, followed by transporting liquid (solvent) as a mobile phase from there, so as to move an aimed substance gradually into the second or subsequent containers. The distribution at the time when the peak of the sample reaches the middle of the system is close to Poisson's distribution when the number of container is small, or to Gauss distribution when the number of container is large. When the head of a necessary component reaches the final container of the system, the separation operation can be continued by connecting newly certain containers containing the same adsorbent and liquid in the same amount.

If a passing speed of liquid, volume of container, the number of containers connected to etc. are properly set up, the amount of an aimed sample in several containers of the starting side can be made in a state of almost none when the aimed sample reaches the last container. Accordingly, these containers of the starting side (upstream side) are removed, and the adsorbent is washed out with solvent having a strong eluting power, followed by equilibrating again with solvent used in the separation, whereby it can be used as a system connecting to the end side (tip side).

Preparing, for example, sixty containers, these are divided into six groups of ten pieces of unit. Fifty pieces are used for the separation procedure and ten pieces are for washing and equilibrating respectively, and by washing and equilibrating ten containers subtracted from the upstream side and successively by connecting to the downstream side end, the number of plates can be increased without limit.

For example, considering Gauss distribution, if an aimed component in the initial sample is taken in about 98% yield, the separation efficiency of that system is to have 100 plates compared to the number of theoretical plates of chromatography. If 6 units are made by 120 containers of two times, the separation efficiency of the system becomes 400 plates, and it becomes 10,000 plates if tenfold containers are used.

Further, in this multistage liquid-solid fractional extraction apparatus, it is possible to analyze a sample taken from an optional position of a container constituting the system or a pipe at an optional time during a separation procedure. It is possible to confirm a separation state and the purity of an aimed component without stopping the separation procedure. Further, since the procedure is only passing of liquid, and rotation or swing of containers, it can easily be automated and an extremely pure substance can be obtained in a necessary amount.

Next, in case of separation of two components, for example, as an optical antipode, the case which needs to carry out a mutual separation can fundamentally be carried our in the same procedure with the above one component system, however at the skirt of both ends it becomes one component because two Gauss distributions become in an overlapped form displacing peaks. Therefore, when a needed purity appears in a tip end part and a rear end part, the part is removed from the system and a system consisting of new other containers is connected to the tip end, followed by a successive separation to make it possible to carry out the separation procedure more rapidly compared with chromatography.

Further, in case of carrying out separation of a racemate, in the center part of the peak of two optical antipodes, there is always a part in which the optical antipodes exist in the same amount, and therefore if it is possible to confirm this part by analysis, it is also possible to carry out automatically the addition of an sample because a racemate which becomes a new resolution object can be added to that part.

In the following, the invention will be illustrated in more detail by way of example, but the invention is not limited to this example. Example A medicine bottle of inner volume 25 ml, manufactured by Iwaki Glass Co., Ltd , was used as a container. To this container was connected two tubes of inner diameter 1 mm, whereby the one was made the inlet part of the mobile phase (liquid), and the other was made the outlet part of the mobile phase (liquid) equipped with filter. 2 g of Amberlite XAD4 (trade name) was introduced into each container as solid for adsorption (adsorbent), and it was packed with 70% methanol as liquid for extraction (extraction liquid) and sealed. This type of 40 containers were prepared, and the inlet part and the outlet part were successively connected in series, followed by installing them to the rotatory stand.

Being associated with rotation of the rotary stand at about 60 rotation/min., the first container was filled with 70% methanolic solution 2 ml containing ethyl p-hydroxybenzoate (concentration 30 g/l) and butyl p-hydroxybenzoate (concentration 60 g/l), followed by starting the extraction by passing 70% methanol at flow rate 4 ml/min. from the side of the first container. During the operation, it was observed in the container that the adsorbent moved in the extraction liquid by subsidence accompanying the change of the up-down direction of the container by rotation.

Figure 4:
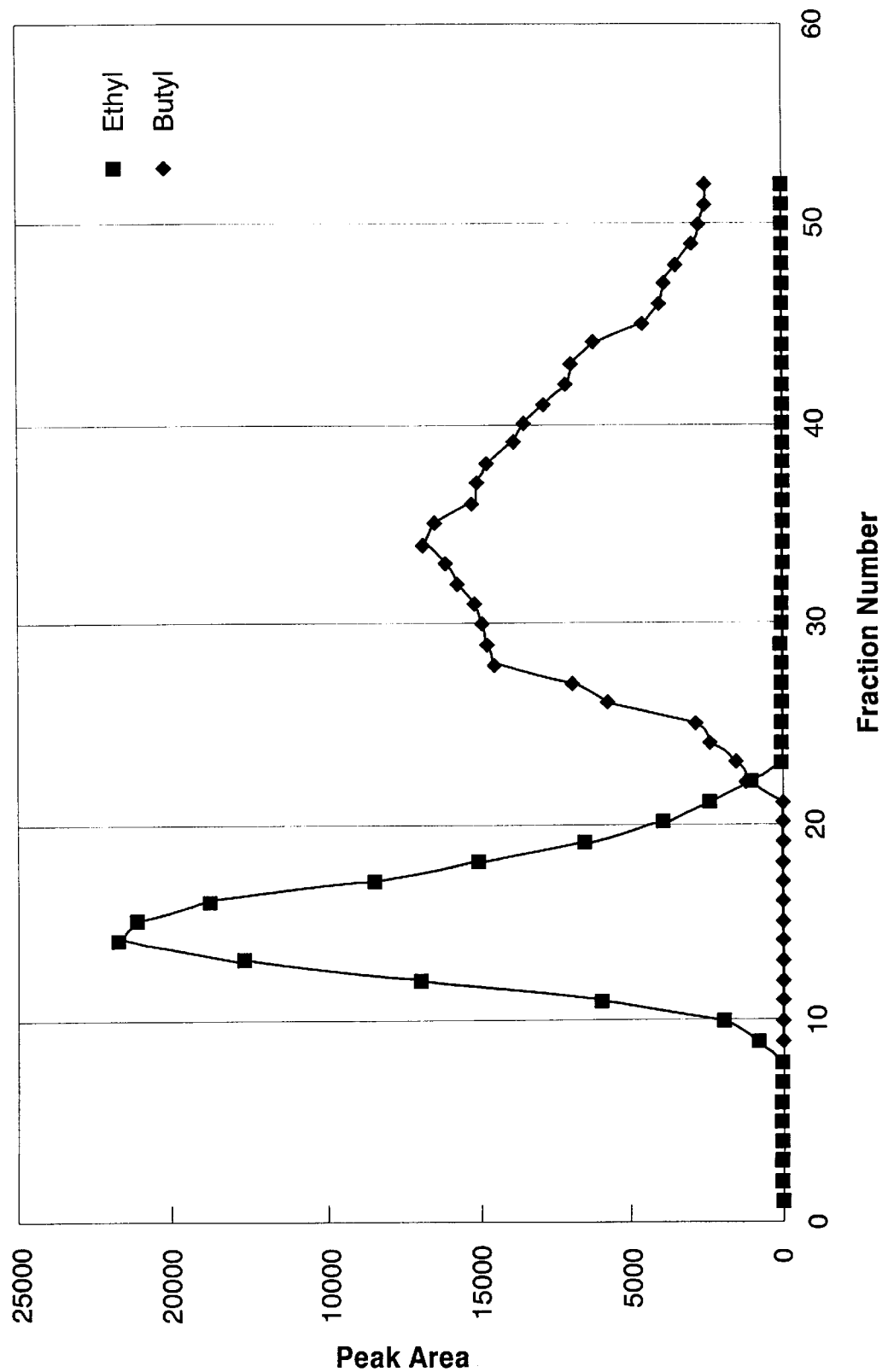
FIG. 4: This shows the results of the example and is the figure representing the peak area of ethyl p-hydroxybenzoate and butyl p-hydroxybenzoate in each fraction.

The elute from the 40th container was fractionated at every 200 ml by use of the fraction collector, and ethyl p-hydroxybenzoate and butyl p-hydroxybenzoate in each fraction were quantified by high pressure liquid chromatography (HPLC). The result is shown in FIG. 4. As is evident from this result, it can be understood that each container corresponds to about one plate of the theoretical plate number of chromatography.

UTILITY OF THE INVENTION

As explained above, a large amount of sample can be separated by the multistage liquid-solid fractional extraction apparatus of the invention as efficiently as by chromatography. Particularly, by use of a density difference between solid and liquid, both are made into a stirred-mixed state by rotation or swing of containers. Therefore, solid is hardly destroyed by friction at the time of stirring, and a large amount of solid mixture can also be stirred efficiently.

Further, since a sufficient stirring and mixing can be carried out regardless of a size or shape of solid, it eases the conditions that adsorbent of a uniform size and shape, which is a necessary condition of chromatography, is used and packed in the column uniformly and a mobile phase is uniformly flowed in the column. Therefore, since it is possible to optionally select a size of a container and also to adjust a volume ratio between solid and liquid at an appropriate proportion for separation of an aimed substance, a separation procedure of a large amount of sample can efficiently be carried out.

What is claimed is:

1. A multistage liquid-solid fractional extraction apparatus comprising multiple containers capable of accommodating liquids and solids subjected to a liquid-solid fractional extraction, each container having a liquid inlet part and a liquid outlet part;

(a) a carrying device to carry the liquid from the liquid outlet part of one container to the liquid inlet part of another container; and (b) a stirring device capable of swinging the containers to change the up-down direction of the containers, such that the solids within the liquid in the containers move by virtue of a density difference between the solids and liquid, (c) wherein at least one liquid outlet part comprises an efflux protecting device for preventing solids from flowing out of the container.

2. The multistage liquid-solid fractional extraction apparatus of claim 1, wherein the apparatus is capable of uniformly mixing the liquids and solids.

3. The multistage liquid-solid fractional extraction apparatus of claim 1, wherein the liquid inlet part of at least one container comprises an influx protecting device for preventing solids from flowing into the container.

4. The multistage liquid-solid fractional extraction apparatus of claim 1, wherein at least one container contains an adsorbent material.

5. The multistage liquid-solid fractional extraction apparatus of claim 1, wherein a sampling device is attached to at least one container.

6. The multistage liquid-solid fractional extraction apparatus of claim 1, wherein the stirring device is a motor or crank.

7. The multistage liquid-solid fractional extraction apparatus of claim 1, wherein the efflux protecting device is a mesh-type filter.

8. The multistage liquid-solid fractional extraction apparatus of claim 1, wherein the apparatus is capable of a liquid flow rate of 4 milliliters per minute through the containers.

* * * * *